(12) United States Patent
Hamilton et al.

(10) Patent No.: US 10,004,843 B2
(45) Date of Patent: Jun. 26, 2018

(54) RADIOPAQUE MARKER TOOL AND METHOD FOR USE IN A RADIOLOGICAL MEDICAL IMAGING PROCESS

(71) Applicants: Brian H. Hamilton, Charlotte, NC (US); Kimberly M. Hamilton, Charlotte, NC (US)

(72) Inventors: Brian H. Hamilton, Charlotte, NC (US); Kimberly M. Hamilton, Charlotte, NC (US)

( * ) Notice: Subject to any disclaimer, the term of this patent is extended or adjusted under 35 U.S.C. 154(b) by 0 days. days.

(21) Appl. No.: 14/814,692

(22) Filed: Jul. 31, 2015

(65) Prior Publication Data

US 2015/0335815 A1    Nov. 26, 2015

Related U.S. Application Data

(63) Continuation of application No. 12/061,869, filed on Apr. 3, 2008, now abandoned.

(51) Int. Cl.
| | |
|---|---|
| *A61B 6/00* | (2006.01) |
| *A61M 5/00* | (2006.01) |
| *A61F 13/40* | (2006.01) |
| *A61B 90/00* | (2016.01) |

(52) U.S. Cl.
CPC ........... *A61M 5/007* (2013.01); *A61B 6/4423* (2013.01); *A61B 90/39* (2016.02); *A61M 35/006* (2013.01); *A61B 6/00* (2013.01); *A61B 6/508* (2013.01); *A61B 2090/3937* (2016.02); *A61B 2090/3995* (2016.02)

(58) Field of Classification Search
CPC ...... A61M 5/007; A61B 90/39; A61B 6/4423; A61B 6/00; A61B 6/508

USPC .... 401/17, 57, 152, 156, 184, 183; 600/424, 600/426, 414; 128/897, 898, 899; 606/116
See application file for complete search history.

(56) References Cited

U.S. PATENT DOCUMENTS

| | | | |
|---|---|---|---|
| 493,464 | A * | 3/1893 | Arthur ................... B43K 21/06 |
| | | | 401/57 |
| 2,106,028 | A | 1/1938 | Heimsch et al. |
| 2,462,018 | A | 2/1949 | Wood |
| 2,596,073 | A | 5/1952 | Graham et al. |
| 3,879,141 | A | 4/1975 | Shulman |
| 4,343,559 | A | 8/1982 | Silver |
| 4,506,676 | A | 3/1985 | Duska |
| 4,813,062 | A | 3/1989 | Gilpatrick |
| 4,860,331 | A | 8/1989 | Williams et al. |
| 4,875,602 | A | 10/1989 | Chickering et al. |
| 4,916,170 | A | 4/1990 | Nambu et al. |
| 5,193,106 | A | 3/1993 | DeSena |
| 5,232,452 | A | 8/1993 | Russel et al. |

(Continued)

*Primary Examiner* — Alexander Valvis
*Assistant Examiner* — Viet Le
(74) *Attorney, Agent, or Firm* — Additon, Higgins & Pendleton, P.A.

(57) ABSTRACT

A marking tool for use in the context of radiological and other medical imaging is disclosed. The product is a marking tool for distributing an imaging material onto a patient's skin to mark that part of the patient's body for imaging. The imaging technician then knows the area of medical interest, such as an internal injury, and can image that area more accurately. The imaging material shows up on a resulting medical image such as an X-Ray, CT Scan, or MRI to direct a radiology professional to the most important area on the image for diagnostic purposes.

19 Claims, 9 Drawing Sheets

(56) References Cited

U.S. PATENT DOCUMENTS

| | | |
|---|---|---|
| 5,357,861 A | 10/1994 | d'Arbelles et al. |
| 5,469,847 A | 11/1995 | Zinreich et al. |
| 5,702,128 A | 12/1997 | Maxim et al. |
| 5,848,125 A | 12/1998 | Arnett |
| 6,179,503 B1 | 1/2001 | Taghavi-Khanghah |
| 6,198,807 B1 | 3/2001 | DeSena |
| 6,254,299 B1 | 7/2001 | Russo |
| 6,333,970 B1 | 12/2001 | LeMaitre et al. |
| 6,459,772 B1 | 10/2002 | Wiedenhoefer et al. |
| 6,689,103 B1 | 2/2004 | Palasis |
| 6,714,628 B2 | 3/2004 | Broyles et al. |
| 6,761,114 B2 | 7/2004 | Koneczny et al. |
| 6,945,172 B1 | 9/2005 | Shih |
| 6,972,008 B2 | 12/2005 | Bills |
| 6,972,022 B1 * | 12/2005 | Griffin .................. A61B 90/39 604/112 |
| 6,985,558 B1 | 1/2006 | Russell |
| 6,991,394 B2 | 1/2006 | Tufts et al. |
| 7,182,541 B1 | 2/2007 | Ziniti et al. |
| 7,226,229 B1 | 6/2007 | Register |
| 7,267,938 B2 | 9/2007 | Anderson et al. |
| 7,731,439 B2 * | 6/2010 | San Miguel ..... A61B 17/00491 401/57 |
| 2004/0127824 A1 | 7/2004 | Falahee |
| 2005/0042015 A1 | 2/2005 | Patel et al. |
| 2006/0241406 A1 | 10/2006 | Noujeim |
| 2006/0266240 A1 | 11/2006 | Ratnakar |
| 2008/0287782 A1 * | 11/2008 | Traboulsi ............... A61B 90/39 600/426 |
| 2009/0253981 A1 | 10/2009 | Hamilton et al. |

* cited by examiner

RADIOPAQUE MARKER TOOL AND METHOD FOR USE IN A RADIOLOGICAL MEDICAL IMAGING PROCESS

CROSS-REFERENCE TO PRIORITY APPLICATION

This application is a continuation of co-pending U.S. patent application Ser. No. 12/061,869 for Skin Marking Tool for Radiological Imaging Material (filed Apr. 3, 2008, and published on Oct. 8, 2009, as Publication No. 2009/0253981 A1). This application incorporates each of U.S. patent application Ser. No. 12/061,869 and U.S. Patent App. Pub. No. 2009/0253981 A1 by reference in their entirety as if set forth fully herein.

FIELD

The invention relates to the field of radiology and includes tools for marking a patient's skin with an imaging material that is radiopaque or, depending upon the type of radiology, otherwise suitable to be visible on the image. The imaging material shows up as a visible indicator on both the patient's skin and the medical image associated with that area of the patient's body. The marking tool assists radiology professionals in achieving the highest quality medical image and in analyzing the image for proper diagnosis.

BACKGROUND

One of the biggest hurdles for a radiologist is the volume of images that must be analyzed every day for diagnostic purposes. Often, these images are collected from remote locations, such as individual physicians' offices or emergency centers. Medical professionals transmit the images to a central radiology unit where trained professionals "read" the image to determine the next course of action for treatment. Radiology professionals face the task of analyzing hundreds of images per day and providing a diagnosis for every patient in a timely manner. This pressure is compounded by the fact that the person reading the image may have no personal communication with the individual patient or with the person who actually performed the imaging. In some cases, the imaging specialist or attending physician sends a note with a brief explanation of the injury being imaged. Often, however, these notes are insufficient to give the radiologist reading the image a clear focus of the exact problem to look for on the multitude of images associated with a patient or group of patients.

As a result, the radiology professional's job is of an extremely broad scope, including the review of many different types of images and particular areas on those images. With better information regarding the actual area of medical interest on an image, the radiologist could focus the review to the most pertinent areas.

There is a need in the radiological arts, therefore, for a product that marks a patient's body to point out the most pertinent area on a corresponding radiological image.

Prior efforts to meet this need have included various attempts to add pointers to medical images. For instance, some imaging professionals place a foreign object on the patient during the scan to emphasize an area of interest to the person reading the image. Unfortunately, foreign objects also bring forth the possibility of obscuring a view of the medical problem on the image. Similarly, various directional arrows are sometimes placed on the image to direct the radiologist to a particular region on the scan. Unfortunately, these can be dislodged inadvertently, pointing to the entirely wrong area.

Still, however, with medical imaging taking on such high tech features as 3-D imaging and higher resolution scanning at various angles, efforts to incorporate directional arrows on an image do not meet the true needs of the radiologist.

Other efforts at marking a radiological image have been set forth in the patent literature and are summarized below.
U.S. Pat. No. 4,813,062 (Gilpatrick '062)

The Gilpatrick '062 patent describes a crayon-like marker composed of substances that are detectable by X-ray examination. Specifically, Gilpatrick discloses a crayon or marking pencil containing a radiopaque substance uniformly dispersed within a waxy medium (e.g., paraffin wax) that is used as a tool for applying a mark to an object for inspection.

The Gilpatrick '062 method for applying a radiopaque marker does not, however, disclose the use of such a device to indicate areas of interest on a medical patient. The stated use of the Gilpatrick device and method is to place a radiopaque mark on a substrate. Specifically, the radiopaque marker is intended for use in the context of textile inspection. Accordingly, Gilpatrick fails to disclose a method for using a radiopaque marker tool in a medical imaging process.

Because the Gilpatrick device is intended for use in textile examination, possible detrimental effects of human contact with certain radiopaque compositions may not have been considered by Gilpatrick. This lack of consideration is evidenced by the fact that the marker disclosed in the '062 patent focuses on compositions containing heavy metals (e.g., bismuth, lead), which in some forms can be toxic to humans.
U.S. Pat. No. 2,462,018 (Wood '018)

The Wood '018 patent also discloses a marker containing a material that is detectable by X-ray examination. Specifically, Wood discloses a crayon or pencil containing fine particles of radiopaque metal atoms in a carrier or vehicle material, such as a wax. Wood alternatively discloses the use of a brush or pen for applying a radiopaque substance in a liquid carrier. The marking device may then be used to apply an X-ray observable mark on the object to be inspected.

Like the Gilpatrick '062 patent, however, the Wood '018 patent discloses a number of heavy metals (e.g., lead, bismuth, uranium, thallium) as the appropriate radiopaque substances. In fact, Wood specifically focuses on lead and limits the list of appropriate materials to elements having an atomic weight of at least 184, which is even greater than the acceptable range noted by Gilpatrick. Thus, Wood likewise fails to disclose a radiopaque marker that is designed to be safe for use on medical patients.

Unlike Gilpatrick, however, the Wood '018 marker is disclosed for use in anatomical X-ray work. The disclosure of the use of the X-ray marker in a medical context is very limited, and appears that the use of the Wood X-ray marker is intended more for marking the plate or film for identification purposes than to mark the patient to pinpoint the site of injury.
U.S. Pat. No. 4,506,676 (Duska '676)

The Duska '676 patent describes a radiopaque identifier for identifying the location of concern on a medical patient so that the examining physician can communicate to an X-ray technician or diagnosing radiologist the area on a radiograph to be analyzed. Specifically, Duska discloses a tape provided with a series of radiopaque markings forming a dashed line along the center of the tape. The radiopaque material disclosed is barium sulfate, but Duska also notes that other pigments or powdered or finely divided material known to be opaque to X-radiation may also be appropriate. Accordingly, Duska discloses the use of safe radiopaque substances applied to a medical patient to identify the location of interest in medical imaging.

Duska does not, however, disclose any tool that applies the radiopaque substance directly to a patient's skin. The patent's disclosure is limited to a tape having radiopaque markings, so the examining physician is limited in the types of marks that can be made by the shape of the tape. Thus, although Duska discloses a radiopaque marking device and system that allows an examining physician to communicate the area of interest to later parties examining the resulting X-ray, the '676 patent fails to provide a better way to mark the skin in a visible manner so that the image is taken of the correct spot and the resulting picture is marked for diagnosing that spot.

U.S. Pat. No. 5,193,106 (DeSena '106)

The DeSena '106 patent describes a device for marking landmarks on the skin as a means of identifying areas of interest under x-radiography. The device involves a radiopaque material affixed to an adhesive tape. The radiopaque material may be formed into a variety of shapes, such as a circle, triangle, or square to provide a marker that encircles the point of interest. The markers are pre-cut and affixed to a roll of tape and distributed from a dispenser, so the markers can be easily dispensed.

DeSena does not disclose a pencil, pen, marker, or any other tool that applies the radiopaque substance, though. Further, the DeSena markers are limited in size and shape to the preformed stickers. In fact, DeSena notes that the markers disclosed are different from prior markers in that they are specifically designed to identify small areas. Accordingly, the examining physician is limited in the markings that can be made and may be especially limited if a relatively large area is the area to be analyzed. Thus, although DeSena discloses another form of radiopaque marker, the '106 patent likewise fails to disclose each and every element of the current invention This review of the pertinent art shows that none of the published material or known products on the market fully address the radiologists' problems of image placement during the patient scanning process or image marking to focus the radiologists' review. The invention herein is, therefore, an important advancement over all prior work in the related fields.

SUMMARY

The invention is a tool and an associated method of distributing a radiopaque material directly onto the skin of a patient in a medical environment to highlight an area of medical interest on a radiological image. The radiopaque material is visible on the patient's skin to assist medical personnel in taking an image of the most useful area for diagnosis. Accordingly, the radiological image shows an area of a patient's body with an opaque marker highlighting the most useful part of the image for diagnosis. The radiopaque material shows up on the image but does not block the view of an underlying internal condition that the patient is experiencing.

In other embodiments, the invention is a tool for distributing the radiopaque material onto the patient's skin. The distribution tools described herein are compact, portable, and useful for more than one application to different patients while maintaining sterility and appropriate hygienic standards. Without limiting the scope of the invention in any way, the tools disclosed herein include technology for swabbing the radiopaque material onto the patient with a disposable applicator, stamping the radiopaque material onto the patient's skin, and drawing on the patient's skin with radiopaque media via an applicator.

DETAILED DESCRIPTION

Figure 1A:
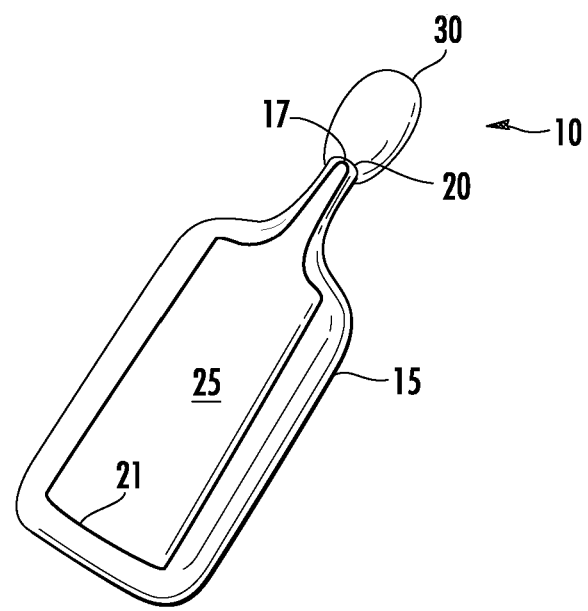
FIG. 1A is a marking tool for applying imaging material directly onto a patient's skin via a swab tip.

The invention is a device and method for marking a patient's body with a suitable substance to identify a location of medical interest, such as the site of a patient's injury. The marking substance, or imaging material, is selected to show up on medical images associated with that patient so that a radiologist or clinician evaluating the images can easily determine the exact site of medical interest. The imaging material further marks the patient's skin to assist the person preparing the image in the first place.

The invention is intended to be used in any setting where medical images are used for diagnosis. Accordingly, the term "medical image" is used in its broadest sense and includes, but is not limited to X-rays, CT scans, fluoroscopy, and MRI technology.

The invention includes the use of specialized substances, referred to herein as "imaging materials" that show up on a medical image to mark the area of medical interest without obscuring the view of important features. The imaging material may be contained in a dispenser capable of placing a small, quick-drying mark on the patient. In a preferred embodiment, the imaging material is visible on the patient's skin to assist the person preparing the patient for imaging in identifying the optimal location. The imaging material has a sufficient concentration to be visible to medical imaging devices (e.g., appears on x-ray films, CT scans, and MRIs), and yet it is not so dense that it obscures the image.

The imaging material is selected based on the type of medical imaging used. For example, compositions containing barium or iodine are suitable for radiographic imaging (i.e., x-ray); dilute iodine-based substances may be appropriate for use with computed tomography (CT); oil based substances, such as Vitamin E or flax seed oil mixtures, and gadolinium compositions are used for magnetic resonance imaging (MRI). In general terms, the imaging material incorporates a substance for highlighting an examination area on both a patient's skin and an associated radiological image. The radiological images include, without limitation, CT scans, MRI, X-ray, and fluoroscopy technology. The invention incorporates the use of any material that is safe for application directly onto a patient's skin and that will show up as a marker on an associated radiological image. Regardless of the application, the imaging material used in this context is safe for skin contact.

The imaging material may be selected from a variety of colors appropriate for the patient's skin tone, the radiologists' goals in providing certain information on the skin, and the availability of particular pigments for the desired application. In the most preferred embodiment, the imaging material should be of a color, consistency, and density that allows the material to dry onto the skin quickly without running or smearing. The imaging material should further be of the appropriate density to show up on a medical image as a marker without completely obscuring the view of the underlying area of medical interest within the patient's body. The imaging materials described herein include versions that are appropriately diluted for use in any particular situation.

The substance may be applied as a liquid or paste dispensed from a device that is convenient to use in a medical setting. The device, or marking tool, may take any form that produces a quick-drying mark that may be quickly and easily placed on the patient without causing any discomfort. In a preferred embodiment of this invention, the marking tool applies the imaging material directly to the patient's skin prior to completing the imaging.

The marking tool (10) may be in the form set forth in the attached figures and the following claims. In a first embodiment, the marking tool (10) includes a substantially hollow vessel (15) for holding the imaging material (13). The marking tools of this invention include a tip (17) at one end of the hollow vessel (15) to define an opening to the interior of the vessel (15) for controlled distribution of the imaging material (13). By using the marking tool (10), a radiology professional can apply an imaging material (13) for distribution through the tip (17) directly onto the patient's skin to mark the examination area.

FIG. 1 shows a more preferred embodiment of the marking tool (10) disclosed herein. In FIG. 1, a marking tool (10) again includes a substantially hollow vessel (15) defining an opening at a first end (20). The marking tool is adapted for distributing imaging material (13) directly onto a patient's skin through a distribution tip (17) fitting within the opening of the hollow vessel (15). The tip (17) is in fluid communication with the interior of the hollow vessel (15) for controlled distribution of the imaging material (13) onto the patient. A closed chamber (25) within the vessel (15) extends from a second end (21) of the substantially hollow vessel (15) toward the opening at the first end (20), and an imaging material (13) is retained within the closed chamber (25).

Figure 1B:
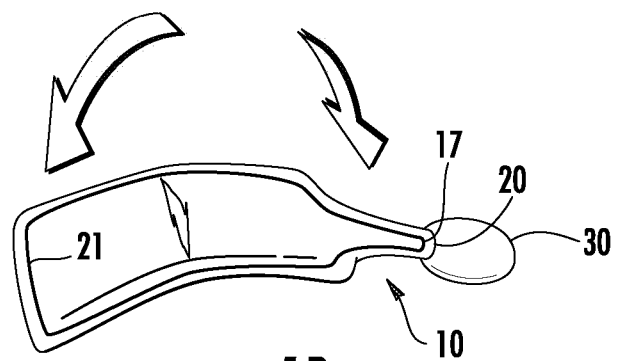
FIG. 1B is an embodiment of FIG. 1A in which the radiopaque imaging solution is housed in a breakable vial within the marking tool of FIG. 1A.

As shown in FIG. 1B, the hollow vessel (15) is pliable for bending, and the closed chamber (25) is breakable upon bending the hollow vessel (15). When the closed chamber (25) breaks, the imaging material (13) is released and flows through the tip (17) of the marking tool (10) for direct dispersion onto a patient's skin.

In a most preferred embodiment of the device of FIG. 1, the tip (17) incorporates applicator (30) (e.g., a swab or wick) that absorbs the imaging material (13) and becomes soaked with imaging material (13) for more comfortable distribution onto the skin. After the imaging material (13) is applied to the skin, the marking tool (10) of FIG. 1 can simply be discarded.

One useful feature of the marking tool (10) is that it is adapted for use with imaging materials (13) that dry or otherwise stay on the skin so that an imaging technician can use the mark to ensure more accurate scanning. Furthermore, the imaging material (13) shows up on the image (usually an X-ray, CT scan, or MRI) for diagnosis by another medical professional. The image on the scan pinpoints areas of medical inquiry to allow a radiologist to focus the review on the most critical areas within an image.

In a different embodiment of FIG. 1, the closed chamber (25) may also be configured to release the imaging material into the hollow vessel by bending both the hollow vessel (15) and the closed chamber (25). In this embodiment, the chamber (25) does not break to release imaging material (13) into the hollow vessel. Instead, the chamber may include a puncture valve at one end. The term "puncture valve" includes, but is not limited to, any hole in the chamber that retains a normally closed ("self-sealed") position, but will allow the imaging material (13) to escape through the hole if the chamber is squeezed or bent. The puncture valve is essentially a hole in the chamber (25) made of a pliable material, e.g., a rubber or other synthetic material, that closes up unless the imaging material (13) exerts enough pressure on the wall of the chamber (25) to force the hole into an opened position. When the pressure from squeezing or bending the chamber (25) is reduced, the material forming the chamber closes upon itself and seals the hole so that no additional imaging material (13) escapes. In this embodiment, the chamber (25) releases the imaging material into the hollow vessel (15), allowing the imaging material (13) to be dispensed through the tip (17) of the marking tool (10), preferably through a swab or wick (30) attached to the tip (17) of the marking tool (10).

Figure 2:
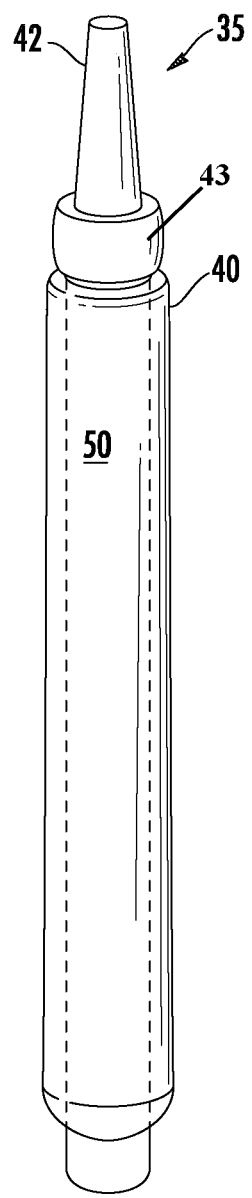
FIG. 2 is a marking tool for applying imaging material directly onto a patient's skin via a squeezable dispenser that does not touch the patient.

FIG. 2 is another representation of the radiological marking tool (35) of this invention. Again, the tool (35) includes a hollow vessel (40) that may either contain the imaging material (13) itself, or it may contain the separate chamber (50) described above for holding the imaging material (13) until dispersion.

Using a separate chamber (25, 50) in any embodiment of this invention may be generally preferred for better control over distribution or for allowing a marking tool (10, 35) to be re-used by simply incorporating a new chamber (25, 50) full of imaging material (13) when the prior chamber runs dry.

As shown in FIG. 2, the hollow vessel (40) of this product may include a distribution tip (42) for marking the patient with imaging material (13). The distribution tip (42) may be a permanently attached article, similar to a highlighter tip, or the distribution tip may be a removable apparatus that would be discarded after a single use on a patient.

Using a removable, disposable tip (42) on the marking tool (35) of FIG. 2 is one preferred embodiment that is useful to prevent contamination between uses on different patients. To further ensure that any germs or contamination on the tip (42) does not backflow into the hollow vessel (40) of imaging material (13), the instrument of FIG. 2 could use a separate chamber (50) of imaging material (13) inside the hollow vessel (40). Any one of the previously described mechanisms for releasing the imaging material (13) into the hollow vessel (40) would work in the device of FIG. 2. In other words, the chamber (50) in the FIG. 2 marking tool (35) could incorporate the puncture valve or a breakable chamber that floods the hollow vessel (40).

Various embodiments of the removable, replaceable tip (42) are also available for use in this embodiment. In the examples of FIG. 1, the distribution tip (42) is of a conical shape for controlling the amount of imaging material that flows out of the hollow vessel (40) onto the patient. For example, the removable tip (42) could be in the form of a nipple that distributes the imaging material (13) upon squeezing or applying pressure. The nipple would be formed of an elastic type of material that is temporarily deformable but pops back into shape.

In a different embodiment of FIG. 2, the chamber (50) may be separated from the tip (42) by a valve assembly (43) that opens and closes by turning the tip (42). For example, by turning the distribution tip (42) in one direction, a normally closed rotating valve assembly (43) may open, allowing the imaging material to flow. After filling the tip (42), the user closes the rotating valve assembly (43) back so that only the imaging material in the tip (42) ever comes near the patient's skin. The valve assembly (43), therefore, prevents back flow contamination from the patient's skin from corrupting the sterility of the imaging material in the chamber (50).

If the chamber (50) incorporated into the device of FIG. 2 uses a puncture valve to control imaging material flow, then the hollow vessel (40) could be configured as a pliable or flexible material that can be squeezed to exert pressure onto the chamber (50).

FIG. 2 is a good example of using squeezable hollow vessels (40) to distribute the imaging material (13). In FIG. 2, the imaging material (13) resides in the bottle-shaped vessel (40) and is easily distributed through a hole in the tip (42). The imaging technician squirts the imaging material directly onto a patient's skin without touching the patient. This distribution method is useful in applications for which a wide distribution of imaging material is sufficient or applications in which just one dot of imaging material will suffice. The hollow vessel (40) of FIG. 2 is sufficiently resilient to resist deformation after being subject to compressive force.

The vessels that house and distribute the imaging material of this invention are in no way limited by the figures and discussions above. The vessel can take the shape of any container capable of distributing the imaging material (13), including but not limited to vessels that squirt or spray the imaging material directly onto the patient. For vessels that spray the imaging material, the invention encompasses all peripheral devices such as straws or nozzles that direct the spray in a desired manner. The vessel, then, includes embodiments such as aerosol containers or pump action bottles configured for the application at hand.

Figure 3:
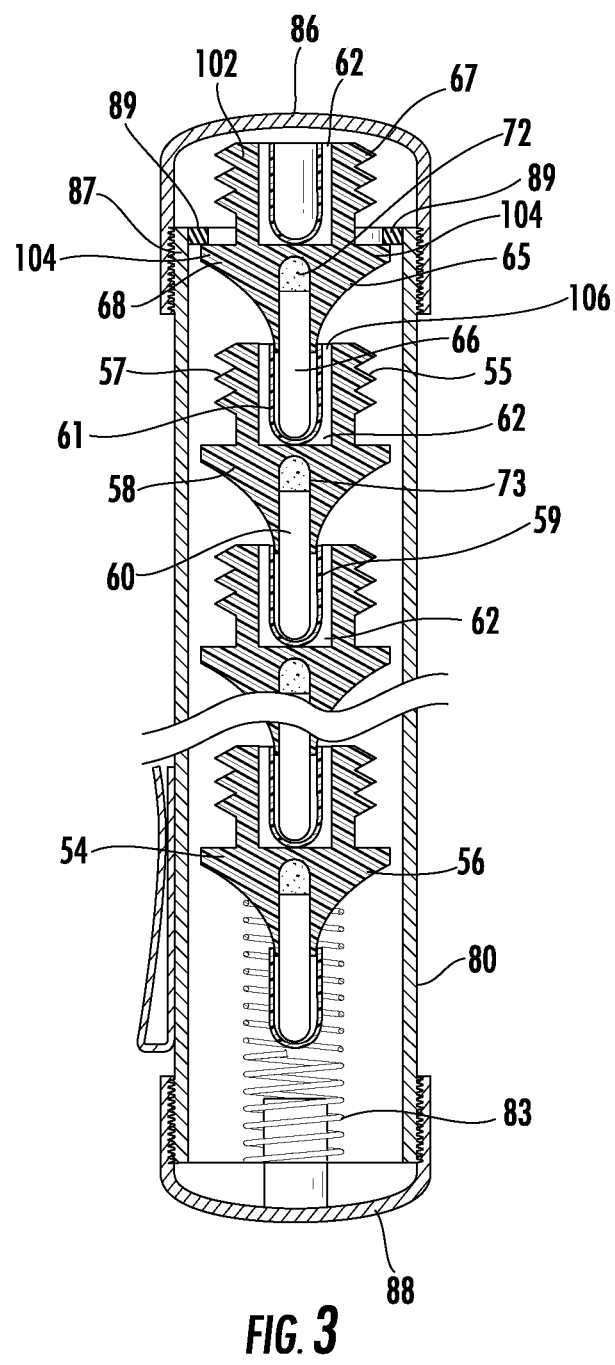
FIG. 3 is a marking tool having a dispensing tip that is pre-soaked with imaging material and stored in a dispenser.
Figure 4:
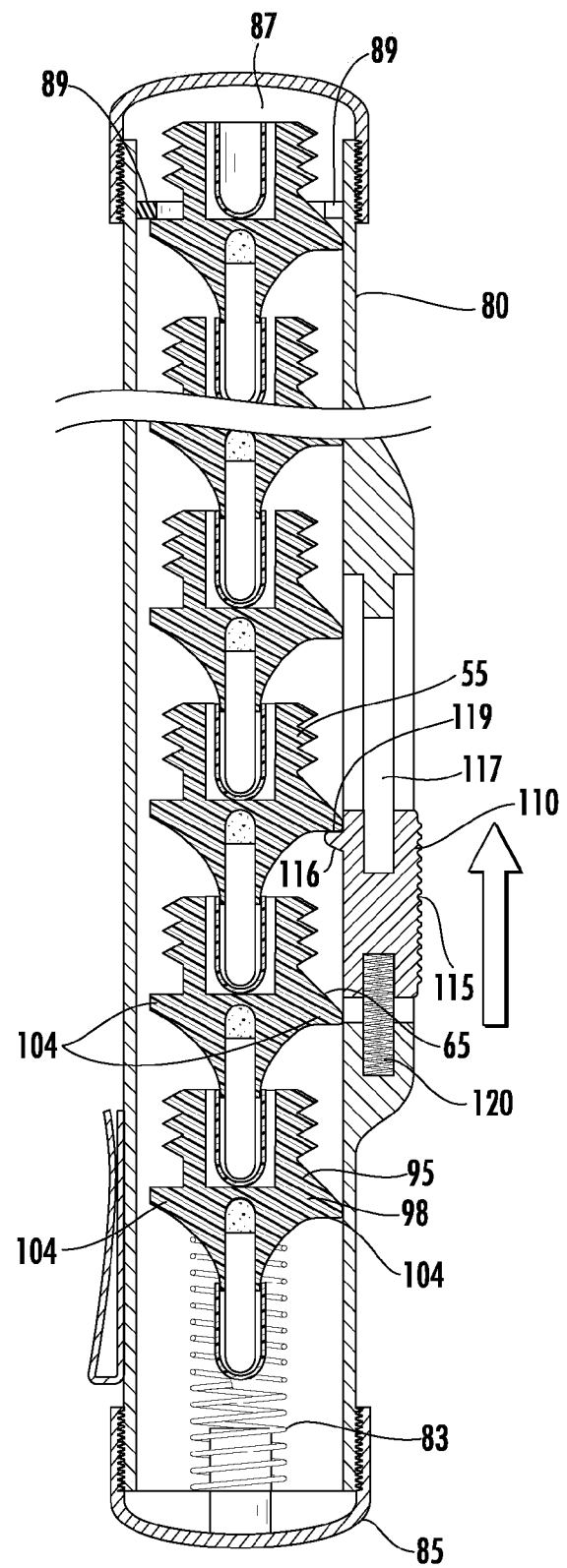
FIG. 4 is a marking tool as in FIG. 3 in which the dispenser has a controlling side-button for pushing out the next marking tool from the dispenser.

FIG. 3 and FIG. 4 show embodiments of the marking tool that are completely disposable after a single use. The marking tool (55) includes a multi-faceted grip (57) attached to a body (58) that holds a wick (60) for distributing the imaging material (13) onto the patient. The grip (57) defines a cavity (62) in which the wick (66) of another marking tool (65) may slide in a nesting configuration. When nested, the wick (66) of one marking tool (65) slides into the cavity (62) of an adjacent grip (57) so that the bodies (58, 68) of at least two marking tools (55, 65) align and connect. In a preferred embodiment, the wicks (60, 66) of each marking tool (55, 65) may be surrounded by a respective sealing cap (61, 59). The sealing cap (61, 59) may be sized to fit within the cavity of an adjacent grip (57) for a secure nesting configuration.

The sealing cap (61, 67) on each wick (60, 66) in FIG. 3 allows for the wicks to be pre-soaked in imaging material (13) for application onto a patient. The pre-soaked wicks (60, 66) maintain their moistness and distribution capabilities because the sealing cap (61) is sufficiently impermeable to prevent evaporation of the imaging material (13). To ensure that each wick (60, 66) is sufficiently soaked with imaging material (13) upon use, the product may include reservoirs (72, 73) of imaging material (13) within the body (58, 68) of the marking tool (55, 65). The wicks (60, 66) then have the reservoir (72, 73) to replenish imaging material (13) that has evaporated due to storage conditions.

The nesting feature of the marking tools (55, 65) shown in FIG. 3 makes the marking tools (55, 65) compatible with a dispenser (80). The dispenser (80) includes a spring (83) that engages the body (56) of a first marking tool (54). The spring (83) is connected to the dispenser (80) and biased to push the nested marking tools (54, 55, 65) outward toward an opposite end (87) of the dispenser (80). At the end (87) of the dispenser (80) opposite the spring (83), the dispenser includes a retention lip (89) that engages the body (68) of a marking tool (65) to be dispensed out of the opposite end (87). The retention lip (89) may be made of a flexible material, such as a rubber or other composite substance, that is sufficiently stiff to retain the nested marking tools (54, 55, 65) within the dispenser (80) even in light of the opposite force of the spring (83).

In the dispenser (80), the retention lip (89) engages the body (68) of the marking tool (65) that is in line for dispensing next. The body (68), therefore, includes the grip (67) with ridges (102) that pass through the retention lip (89). The body (68) of the marking tool (65), however, engages the retention lip (89) and rests against the lip (89). In this embodiment, the body (68) of the marking tool (65) includes a protrusion (104) that is sufficiently wide for the retention lip (89) to hold the body (68) back. As shown in FIG. 3, at this point, the grip (67) pushes past the retention lip (89) and is available for manual removal. The remainder of the body (68) remains on the opposite side of the retention lip (89) within the dispenser (80). A dispenser cap (86) is available to close off the marking tools from the outside elements, further protecting the individual wicks (60, 66) from evaporation.

In use, then, the dispenser of FIG. 3 allows radiology professional to remove the dispenser cap (86), manually pull the grip (67) of the marking tool (65) up for dispensing, and remove the body (68) of the marking tool (65) past the retention lip (89). The marking tool (65) is then retrieved from the nested series of marking tools in the dispenser (80). In one embodiment, the retrieved marking tool is removed with its wick sealing cap (106) remaining in the grip cavity of the immediately adjacent marking tool. In other embodiments, the entire marking tool, including the sealing cap (106) is removed, and the radiology professional removes the wick sealing cap for disposal. The dispenser (80) may be of any size and shape that is useful to dispensing the marking tools. For example, and without limiting the invention, the dispenser (80) may be shaped similarly to a pen and conveniently fit inside the user's jacket or shirt pocket. For this embodiment, the dispenser (80) includes a pocket clip (82) for ease of retrieval. The marking tool of FIG. 3 incorporates a removable loading cap (88) attached to the spring (83). The user can unscrew the removable loading cap (88), pull out the spring, and insert more nested marking tools therein.

The embodiment of FIG. 4 includes all of the above discussed elements from FIG. 3 with the addition of a side button (110) for pushing the marking tools (55, 65, 95) through the retention lip (89). As noted in regard to FIG. 3, the body (98) of the marking tool (95) has a protrusion (104) that engages the retention lip (89) and prevents the spring (83) from pushing the marking tool (95) out the opposite end (87). In the embodiment of FIG. 4, the dispenser (80) is equipped with a side button (110) that includes an exterior component (115) that slides along a rail (117). The side button further includes an interior component (116) in the form of an edge (119) that engages the protrusion (104) of a marking tool (95). The side button (110) engages a recoil spring (120) that is biased to expand in the opposite direction as the dispenser spring (83). The user manually pushes the side button (110) in the direction of the arrow shown in FIG. 4 to push one of the marking tools (95) out of the dispenser (80). The recoil spring (120) pulls the side button (110) back away from the dispensing, or opposite end (87). The nested marking tools move in response to the spring (83) and the recently dispensed marking tool removal such that the protrusion (104) on the body (98) of a marking tool closer to the spring (83) is forced over the interior component, or edge (116, 119), of the side button. In this way, the series of nested marking tools advance down toward the dispensing end (87) of the dispenser (80) in an orderly and controlled way.

The embodiments depicted in FIGS. 3 and 4 are useful in the way that each marking tool (55, 65, 95) is dispensed individually for single use and disposal. The spring (83) end of the dispenser also may include a loading cap (85) that is removable, such as a screw cap. The loading cap and spring assembly can be removed, allowing for reloading the dispenser with additional marking tools.

Figure 5A:
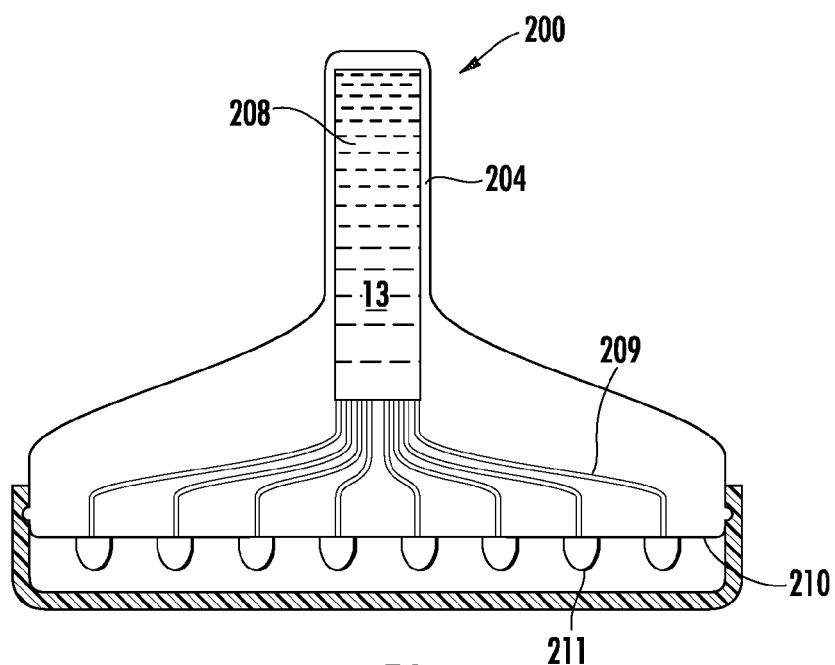
FIG. 5A is a marking tool for stamping an imaging material directly onto a patient's skin in a certain pattern for use by a radiologist.
Figure 5B:
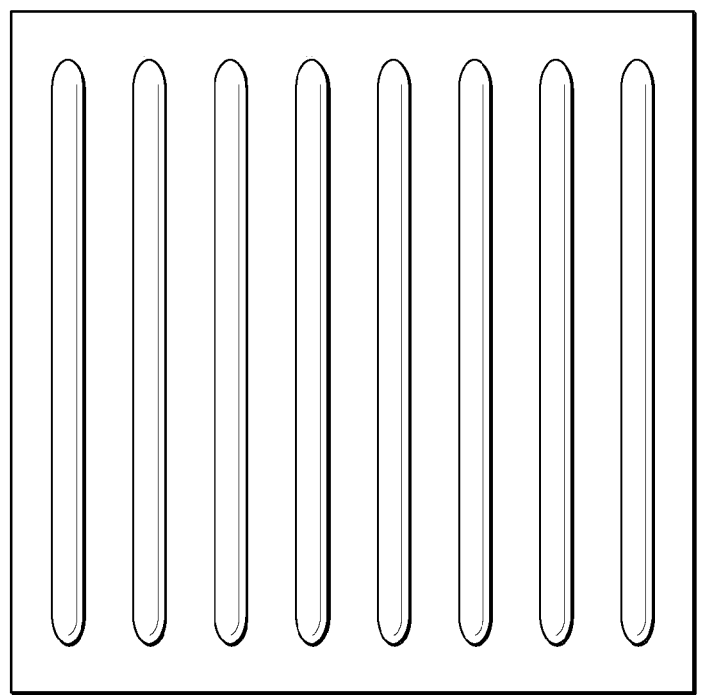
FIG. 5B is a bottom view of the marking tool of FIG. 4*a* showing one associated stamp pattern in the form of a grid.
Figure 5C:
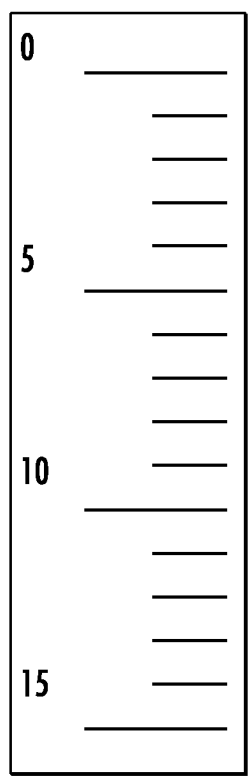
FIG. 5C is a bottom view of a marking tool in the form of a stamp that forms a ruler image on a patient's skin.
Figure 5D:
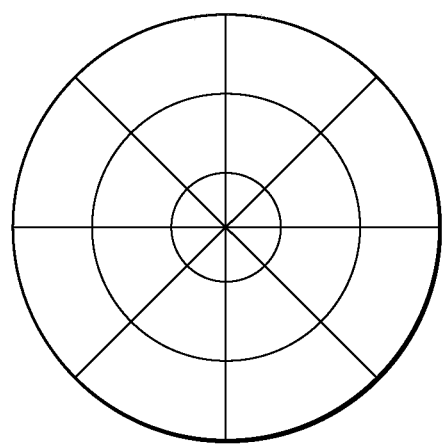
FIG. 5D is a bottom view of a marking tool in the form of a stamp that forms a target image using concentric circles and radiating sectors.

The next embodiment of the marking tool according to this invention is shown in FIGS. 5A and 5B. In this embodiment, the marking tool (200) includes the hollow vessel (204) and closed chamber (208) embodiment discussed above. In addition, however, the marking tool (200) includes a mechanism for moistening a stamp pad (210) in fluid communication with the imaging material (13) released from the chamber (208) or the hollow vessel (204). The stamp pad may include numerous designs as shown in FIGS. 5B, 5C, and 5D.

In the embodiment of FIG. 5A, the marking tool (200) has capillaries (209) that moisten multiple regions of a stamp pad (210). Other embodiments may not require such extensively controlled imaging material flow, and the capillaries may be replaced with any conduit for moving the imaging material from the hollow vessel to an attached stamp pad.

In using the marking tool (200) of FIG. 5A, the radiology professional soaks an attached stamp pad (210) with imaging material housed in the hollow vessel (204). The soaking step may be accomplished in many ways, including breaking a closed chamber (208) of imaging material within the hollow vessel (204) or squeezing the hollow vessel (204) to release the imaging material (13) onto the stamp pad (210). In the drawing of FIG. 5A, the user would squeeze the hollow vessel (204) to push the imaging material (13) through the capillaries (209) onto an attached stamp pad (210). Once the stamp pad is sufficiently moistened with imaging material, the user would stamp a design of imaging material onto the patient's skin. To accomplish the desired marking, the stamp pad (210) includes moistened raised ridges (211) that have been flooded with imaging material and release that imaging material upon contact with the skin. As shown in FIG. 5A, the capillaries direct the imaging material to the raised, or patterned, portions of the stamp pad (210).

The marking tool of FIG. 5A may be a one-time use instrument, but the product encompasses those marking tools that have replaceable stamping pads on the bottom of the marking tool. In one embodiment, the stamping pads are attached as a peeling stack in which each used stamping pad is removed individually after use. To ensure sterility of use, the stamping pad may be formed in a stack in which each individual pad is peeled off from the adjacent pad, leaving behind a release layer that ensures that the remaining pad is sterile.

The patterns are in no way limited to any one design. Useful designs include, but are not limited to, grids as shown in FIG. 5B. These grids are helpful to a radiologist conducting a CT-guided biopsy in which the imaging material shows up on the image as well as the patient's skin. The radiologist evaluates the internal position of a mass to be biopsied, the design of imaging material distributed onto the skin, and the position of that design in relation to the mass on the patient's medical image. The radiologist then directs the needle or other medical instrument to the most accurate location for treatment. The invention further encompasses a stamp, such as that of FIG. 5C, that prepares an examination area with marked measurements. In a separate embodiment, the imaging material can form a tattoo-like ruler on the patient's skin so that the radiologist can determine distances in certain diagnostic environments, such as angiographic procedures, with more accuracy. FIG. 5D is a useful design for breast tissue biopsies in which a circular target type of design is divided into sectors formed from radiating segments.

Figure 6A:
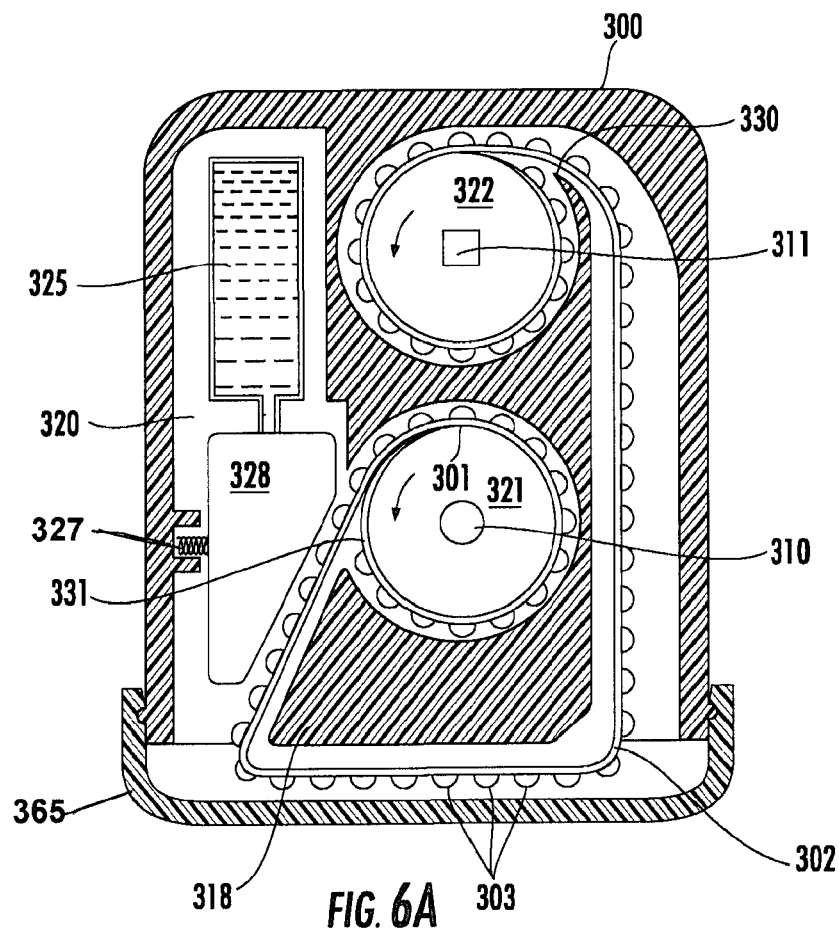
FIG. 6A is a cross-sectional view of an imaging material dispenser in which stamping designs are reeled on winding tape and soaked in imaging material during use.
Figure 6B:
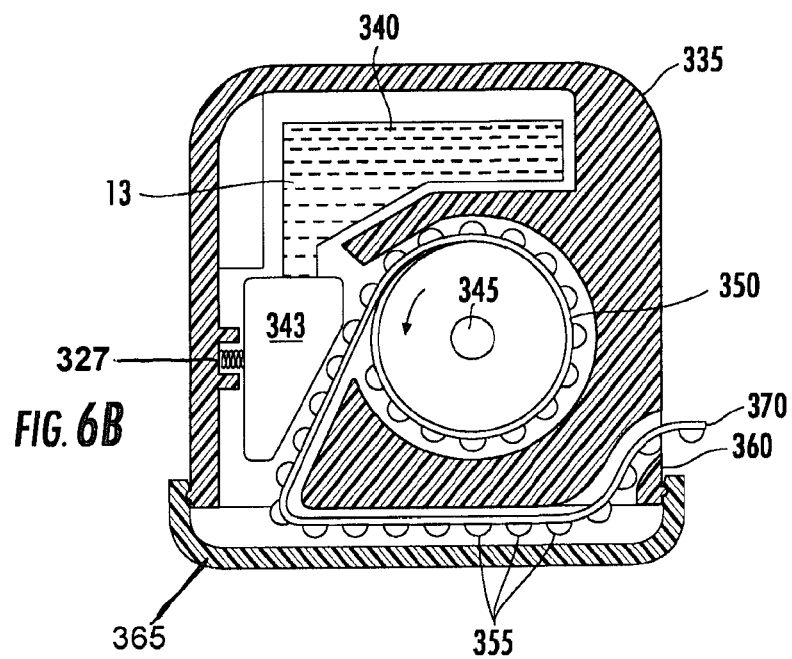
FIG. 6B is a cross-sectional view of an imaging material dispenser in which stamping designs are reeled on winding tape soaked in solution and torn off for discarding.

FIGS. 6A and 6B include yet another embodiment of a marking tool (300) according to this product for dispensing imaging material (13) onto the patient. In regard to FIG. 6A, a desirable stamping design is formed onto a patterned tape (302) in which the pattern is formed of absorptive material that readily soaks with imaging material (13). The tape (302) may include any useful and desirable pattern in the form of raised ridges (303) on the tape (302). The ridges (303) are particularly spongy and absorptive to imaging material (13) while the portions of the tape between the ridges (303) is less absorptive or not absorptive to imaging material at all. In this embodiment, the ridges (303) are designed to absorb imaging material onto the patterned part of the tape (302) and release the imaging material (13) when the ridges (303) are squeezed against a patient's skin.

In one embodiment, the marking tool of FIG. 6A includes a stamping body (318) that is substantially firm to press against the patient's skin. The stamping body (318) defines multiple cavities in which operational parts of the marking tool fit. A first cavity (320) houses an imaging material reservoir (325) that is in fluid communication with a sponge (328). The reservoir (325) of imaging material (13) maintains the sponge in a saturated state. A second cavity (321) within the stamping body houses a dispensing rolling bar (310). In this embodiment, the tape (302) is formed into a concentrically wound roll (301) that can be attached to the dispensing roller bar (310) within the marking tool (300). The dispensing roller bar (310) is positioned within the second cavity (321) defined by the stamping body (318) of the marking tool (300). The stamping body (318) further defines a third cavity (322) in which a take-up roller bar (311) allows for used portions of the patterned tape (302) to wind up after use. The cavities (320, 321, 322) are accessible for replenishing the imaging material (13), the reservoir (325), the sponge (328), or the patterned tape (302). The roller bars (310, 311), can be wound with handles (not shown) or even automated take up gears.

In operation, the marking tool (300) is useful for pressing the stamping body (318) onto the patient's skin with the patterned tape (302) between the stamping body and the skin. In this way, the ridges (303) on the patterned tape (302) release the imaging material (13) absorbed therein and form a pattern of imaging material (13) onto the patient. Again, the pattern of imaging material is visible to the technologist setting up and operating the imaging machinery. The imaging material (13) pattern also shows up on the associated medical image without obscuring the underlying medical condition.

To use the marking tool (300) of FIG. 6A, the radiological technician would wind the patterned tape (302) to marked positions on the tape. The marked positions indicate the length of tape necessary to completely prevent any contamination from one use to the next. In other words, the length of patterned tape (302) extending from the dispensing roller (310) to the take-up roller (311) is sufficiently long to ensure complete disposal of any portion of the patterned tape (302) that has been previously exposed to another patient. For example and without limiting the invention, one desirable length of tape for a single use may extend between points (330) and (331) on FIG. 6A.

After rolling the patterned tape (302) to the appropriate marked positions, the patterned tape (302) from the dispensing roller (310) passes in compressed engagement with the sponge (328) soaked with imaging material (13). The degree of compression between the patterned tape (302) and the sponge (328) is sufficient to soak completely the ridges (303) that form the pattern on the tape (302). For a clear image on the patient's skin, the degree of compression between the patterned tape (302) and the sponge (328) should minimize the amount of imaging material dispersed on portions of the patterned tape (302) other than the design ridges (303). The amount of compression is controlled by a spring (327) connected to the body of the marking tool (300) and pushing against the sponge (328). The spring (327), therefore, biases the sponge to remain in contact with the patterned tape (302). By winding the take-up roller (311), the dispensing roller (310) moves in conjunction to pull the patterned tape (302) across the saturated sponge to allow the absorbent ridges (303) to become fully engorged with imaging material (13). Once the patterned tape (302) has been placed in proper position, the user presses the stamping body (318) against the patient's skin. The stamping body (318) exerts sufficient compressive force on the patterned tape (302) so that the ridges (303) expel the imaging material (13) onto the patient's skin in a desirable imaging pattern.

The embodiment of FIG. 6B operates according to the same principles discussed in regard to FIG. 6A with the exception that FIG. 6B excludes the take-up roller bar (311). Instead, according to the embodiment of FIG. 6B, the marking tool (335) has appropriate cavities to house the imaging material reservoir (340), the sponge (343), and one dispensing roller (345) for a wound patterned tape (350). The patterned tape (350) has a desirable marking image formed by raised ridges (355). The difference in FIG. 6B is that the used patterned tape (350) can be torn off by a razor assembly (360). In this embodiment, then, the user winds the dispensing roller (345) or simply pulls on the free end (370) of the patterned tape (350). Once the tape (350) is pulled to the appropriate length, which may be marked as noted in regard to FIG. 6A, the user can tear off the excess or previously used tape for discarding. This embodiment also ensures that the raised ridges (355) are saturated with imaging material (13) by passing the ridges (355) on the patterned tape (350) across the sponge with sufficient compressive force between the sponge and the ridges (355) to allow for the ridges (355) to absorb imaging material. The user then presses the marking tool (335) against the patient's skin so that the ridges (355) release the imaging material (13) in a known pattern onto the skin.

The patterned tape (302, 350) of both FIGS. 6A and 6B includes marks to ensure that a sufficient strip is discarded after each use to maintain sterility. In one embodiment, the patterned tape (302, 350) is perforated or includes other indicators to show the user how far to wind the tape or how long of a strip should be torn off prior to each use. This feature maximizes sterility and ensures that the patterned tape has a sufficient amount of imaging material on the pattern for use.

Both embodiments shown in FIGS. 6A and 6B include a cap (365) to prevent the imaging solution from drying during periods of non-use. The cap (365) further enables a medical professional to cover the marking tool (300, 335) for conveniently carrying the device in a pocket without staining. In one embodiment, the marking tool (300, 335) is of a convenient shape and size to be portable in a shirt or jacket pocket.

Figure 7A:
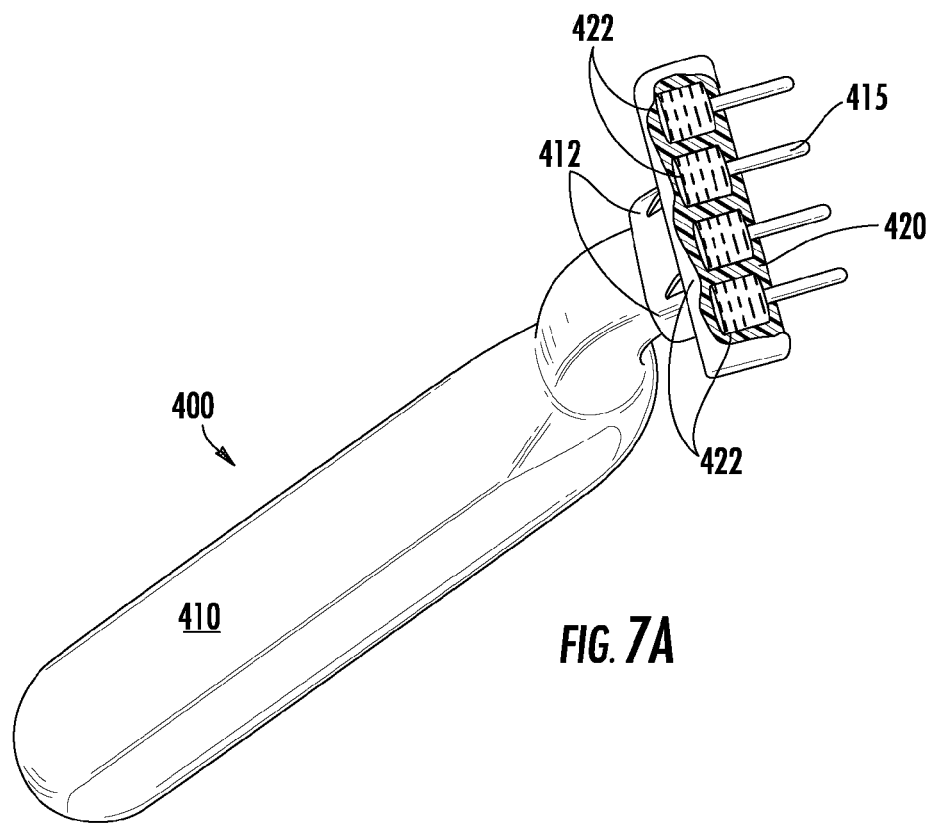
FIG. 7A is a plan view of an imaging material dispenser having pre-soaked wicks with imaging material reservoirs in the dispensing head attached to a handle.
Figure 7B:
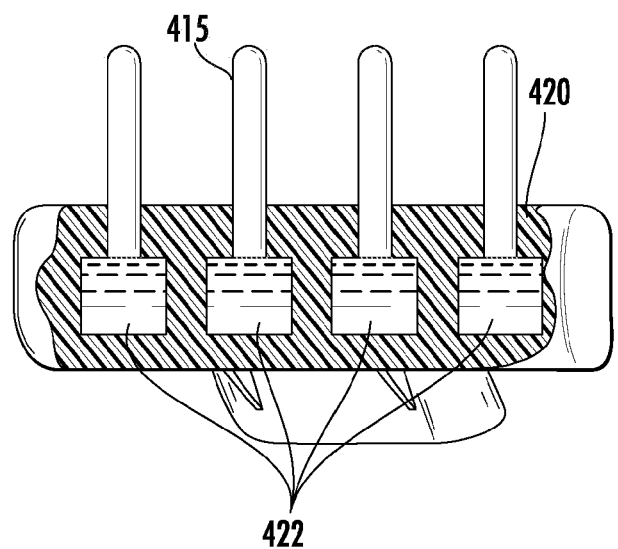
FIG. 7B is a side view of the imaging material dispensing head according to FIG. 7A.
Figure 7C:
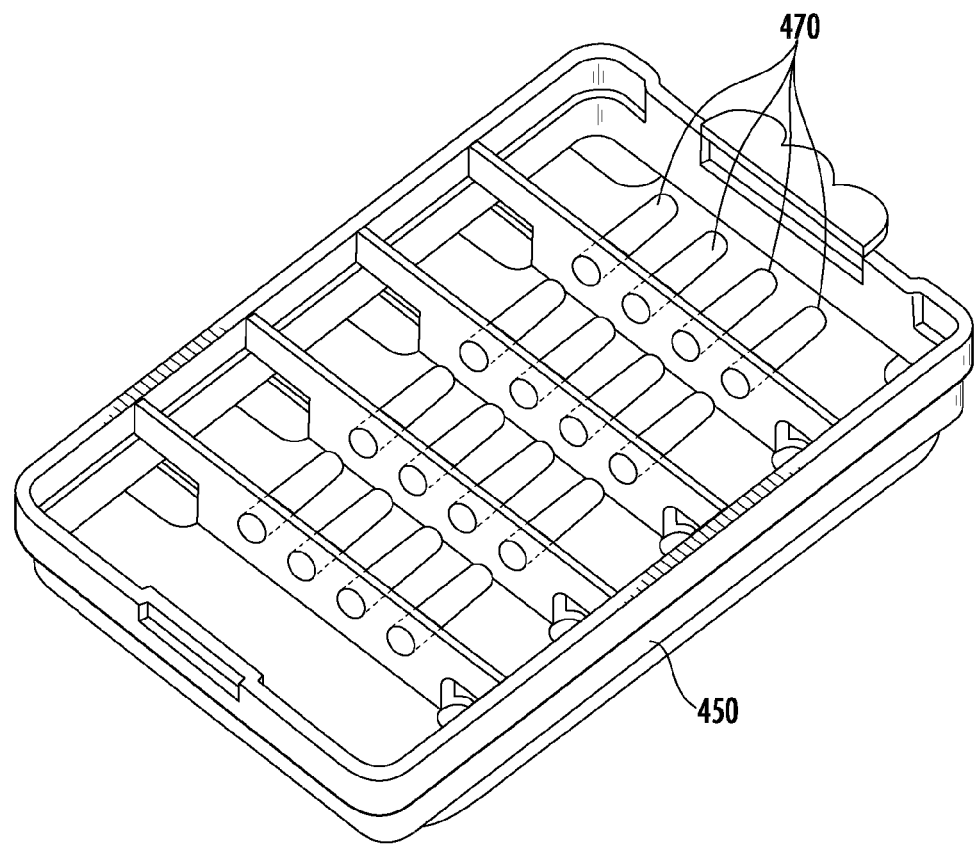
FIG. 7C is a plan view of a cartridge for holding and dispersing multiple imaging materials dispensing heads shown in FIGS. 7A and 7B.

FIGS. 7A to 7C show yet another embodiment of a marking tool useful for radiological purposes. The marking tool (400) is a hand-held instrument with a handle (410) at one end and a releasable marking head (420) at the other end. The marking head (420) clips onto the handle (410) for use and is removable by squeezing a release lever (412) on the top of the handle (410). The release lever (412) moves up and down to engage and disengage a corresponding engagement bevel (413) within the marking head (420).

The marking head (420) includes multiple wicks (415) that are soaked in imaging material (13). To ensure that the marking head wicks (415) remain saturated during periods of storage, the marking head (420) includes imaging material reservoirs (422) in fluid communication with each wick (415) to constantly supply imaging material to the wicks. FIG. 7A shows only one possible configuration for the wicks, as any shape or desired number of wicks will serve the same purpose. In fact, if necessary, the marking head could have just one wick that extends along the width of the marking head (420) or multiple designs on the edges of each wick (e.g., pointed wicks, rounded wicks, jagged wicks) for other marking capabilities.

To ensure that the handle (410) is reusable, the marking heads may be stored and sold in the cartridge format of FIG. 7C. The cartridges (450) hold multiple marking heads (420) and seal the pre-soaked wicks (415) in an appropriate storage chamber (470) to maintain saturation. When one marking head (420) is used up or dried out, then the lever (412) on the handle (410) can release the marking head (420) for disposal. The user then inserts the handle (410) into the neck of the marking head (420) so that the handle lever (412) engages the bevel (413) inside the marking head to retrieve the marking head (420) on the handle (410) for use. At this point, the radiology professional can use the wicks (415) on the marking head (420) to mark areas of interest on the patient's skin by applying the imaging material in a desirable pattern.

The invention herein is sufficiently broad to account for various other means of applying the imaging material to skin stamp. Of course, a traditional ink pad could be used in conjunction with the marking tool by pressing the marking tool with a skin stamp thereon against a pad soaked with imaging material. In this embodiment, an entire stack of skin stamps could be affixed to the bottom of the marking tool, one attached to the other with a releasable adhesive. As the bottom stamp is used, that skin stamp is peeled away and the next skin stamp is made available. To ensure complete sterility, the invention may include a release layer, or peel away strip of paper, between each skin stamp.

In a marking tool according to this invention, the skin stamp comprises a uniform design of raised ridges for placing a planned pattern of imaging material directly onto a patient's skin. When that pattern is retained on the skin by drying or otherwise, the radiologist will have a mapping diagram visible on the skin to plan medical intervention with needles or other tools. When a medical imaging test is performed on the patient, the imaging material design also shows up on the image to inform the radiologist even further in treating the patient. This is especially useful in tracking imaging material position on the skin with the imaging material that shows up on the medical image. For example, if the imaging material is placed on the skin in a series of visible hash marks, those same marks will show up on the image to help the radiologist pinpoint better locations of medical interest by counting the marks.

The invention herein is adaptable to multiple tools that implement this new method of indicating an examination area on a patient's medical images by distributing imaging material directly onto the patient's skin. The descriptions of the embodiments noted above are in no way limiting of the devices that could be used to form radiological markings directly onto a patient's skin. Many different adaptations of this invention are available to ensure that a patient is marked with imaging material forming patterns on the skin that are visible on the patient and visible on the medical images associated with that patient's medical condition. The invention is further intended for all medical purposes, including but not limited to treatment of the human population as well as veterinarian applications.

Those having skill in the art will recognize that the invention may be embodied in many different types of hollow vessels with distribution tools for imaging material. For example, the invention described herein may be adjusted for use in a sterile environment such as an operating room or a clean-room portion of a laboratory. Accordingly, the invention is not limited to the particular structures illustrated herein.

In the drawings and specification there has been set forth a preferred embodiment of the invention, and although specific terms have been employed, they are used in a generic and descriptive sense only and not for purposes of limitation, the scope of the invention being further defined in the claims.

The invention claimed is:

1. A system for indicating an examination area on skin and associated medical images, comprising:
   marking tools, the marking tools comprising:
      a wick containing imaging material; and
      a grip having a body that holds the wick for distributing the imaging material from the wick onto a patient's skin to indicate an examination area at an area of medical interest and on associated medical images; and
   a dispenser, the dispenser comprising:
      a substantially hollow vessel defining an opening at a first end, configured to engage the marking tools when a series of marking tools are placed in the dispenser;
      a resilient mechanism within the substantially hollow vessel for engaging the marking tools to push the marking tools to the opening at the first end;
      a button including an exterior component and an interior component, the interior component configured to releasably engage the marking tools in the dispenser, and the exterior component configured to allow a user to selectively advance the marking tools within the dispenser; and
      a recoil mechanism in operative engagement with the button, the recoil mechanism configured to pull the button away from the first end when a user selectively advances the marking tools within the dispenser.

2. The system according to claim 1, wherein the marking tools comprise a cap surrounding a base portion of the wick.

3. The system according to claim 2, wherein the resilient mechanism comprises a compression spring.

4. The system according to claim 3, wherein the recoil mechanism comprises a recoil spring.

5. The system according to claim 4, wherein the imaging material comprises barium, iodine, an oil-based compound, or gadolinium; and
   wherein the dispenser comprises a removable cap at a second end of the vessel for inserting the marking tools into the dispenser.

6. The system according to claim 1, wherein the medical image comprises an MM, X-Ray, CT scan, or fluoroscopic image.

7. A method for indicating a medical examination area on a patient's body and on associated medical images of the examination area with a dispenser comprising a substantially hollow vessel having an opening at one end, the vessel holding a series of nested marking tools, the marking tools including (i) a wick containing imaging material, and (ii) a grip having a body that holds the wick, the method comprising:
   identifying an area of medical interest on a patient's body;
   selectively dispensing, via an exterior component of a button on the dispenser, a marking tool of the series of marking tools positioned closest to the dispenser opening from the dispenser;
   pulling, via a recoil mechanism of the dispenser, the button away from the one end of the dispenser in response to the marking tool positioned closest to the opening being selectively dispensed;
   distributing, using the grip of the dispensed marking tool, the imaging material from the wick directly onto the identified area of medical interest creating a visible mark that highlights an examination area on the patient's body;
   taking a medical image of the visibly marked examination area wherein the imaging material visibly highlights the examination area on the medical image; and
   providing the medical image for a diagnosis of the visibly highlighted examination area.

8. The method according to claim 7, wherein the button on the dispenser comprises an interior component releasably engaging the marking tools in the dispenser, and wherein the recoil mechanism is in operative engagement with the button.

9. The method according to claim 8, wherein the marking tools comprise a cap surrounding a base portion of the wick and housing imaging material in fluid communication with the wick allowing imaging material into the wick for distribution onto the patient's skin.

10. The method according to claim 9, wherein the imaging material is selected from the group consisting of barium, iodine, an oil based compound, and gadolinium.

11. The method according to claim 10, wherein the medical image is selected from the group consisting of an MM, X-Ray, CT scan, and fluoroscopic image.

12. The method according to claim 11, wherein the imaging material comprises a composition selected from the group consisting of barium sulfate, bound iodine, flax seed oil, Vitamin E, and gadolinium.

13. The method according to claim 7, wherein the area of medical interest on the patient's body is the site of an internal injury.

14. An apparatus for indicating an examination area on skin and associated medical images, comprising:
 a dispenser comprising a substantially hollow vessel defining an opening at a first end, the vessel holding a series of nested marking tools, the marking tools comprising:
  a wick containing imaging material; and
  a grip having a body that holds the wick;
 wherein the dispenser is configured to engage the marking tools and advance the marking tools within the dispenser to the opening at the first end to allow removal of a marking tool of the series of marking tools positioned closest to the opening;
 wherein the dispenser comprises a button for selectively dispensing the marking tool positioned closest to the opening; and
 wherein the dispenser comprises a recoil spring in operative engagement with the button, wherein the recoil spring is configured to pull the button away from the first end when a user dispenses the marking tool positioned closest to the opening.

15. The apparatus according to claim 14, wherein the marking tools comprise a cap surrounding a base portion of the wick.

16. The apparatus according to claim 15, wherein the dispenser includes a dispenser spring within the substantially hollow vessel for engaging the marking tools.

17. The apparatus according to claim 16, wherein the dispenser comprises a removable cap at a second end of the vessel for inserting the marking tools into the dispenser.

18. The apparatus according to claim 17, wherein the imaging material is selected from the group consisting of barium, iodine, an oil based compound, and gadolinium.

19. The apparatus according to claim 17, wherein the medical image is selected from the group consisting of an MM, X-Ray, CT scan, and fluoroscopic image.

* * * * *